United States Patent [19]

Amselem et al.

[11] Patent Number: 5,662,932

[45] Date of Patent: *Sep. 2, 1997

[54] SOLID FAT NANOEMULSIONS

[75] Inventors: Shimon Amselem, Rehovot; Doron Friedman, Carmei Yosef, both of Israel

[73] Assignee: Pharmos Corporation, New York, N.Y.

[*] Notice: The term of this patent shall not extend beyond the expiration date of Pat. No. 5,576,016.

[21] Appl. No.: 697,704

[22] Filed: Aug. 27, 1996

Related U.S. Application Data

[63] Continuation of Ser. No. 63,613, May 18, 1993, Pat. No. 5,576,016.

[51] Int. Cl.$^6$ .............................. A61K 9/127; A61K 9/16
[52] U.S. Cl. .................... 424/450; 424/489; 424/490; 424/502; 424/45; 428/402.2; 514/937
[58] Field of Search .......................... 424/450, 489, 424/490, 497, 45, 502; 514/937–943; 428/402.2

[56] References Cited

U.S. PATENT DOCUMENTS

| | | | |
|---|---|---|---|
| 5,023,271 | 6/1991 | Vigne | 514/458 |
| 5,171,737 | 12/1992 | Weiner | 514/3 |
| 5,188,837 | 2/1993 | Domb | 424/450 |
| 5,284,663 | 2/1994 | Speaker | 424/489 |
| 5,302,401 | 4/1994 | Livesidge | 424/501 |
| 5,306,508 | 4/1994 | Kossovsky | 424/493 |
| 5,308,624 | 5/1994 | Maincent | 424/427 |
| 5,576,016 | 11/1996 | Awalem | 424/450 |

FOREIGN PATENT DOCUMENTS

| | | |
|---|---|---|
| 0 315 079 | 5/1989 | European Pat. Off. . |
| 0 506 197 | 9/1992 | European Pat. Off. . |
| 91/07171 | 5/1991 | WIPO . |

OTHER PUBLICATIONS

CRC Press, Inc., Liposome Technology, 2nd Edition, vol. 1, Chapter 28, p. 501, Liposome Preparation and Related Techniques, edited by Gregory Gregoriadis, Ph.D., "A Large–Scale Method For The Preparation Of Sterile And Nonpyrogenic Liposomal Formulations Of Defined Size Distributions For Clinical Use", by Shimon Amselem, Alberto Gabizon, and Ychezkel Barenholz.

Methods of Biochemical Analysis, vol. 33, D. Glick, editor, J. Wiley & Sons, N.Y., 1988, "Liposomes: Preparation, Characterization, and Preservation", Dov Lichtenberg and Yechezkel Barenholz.

Journal of Pharmaceutical Sciences, vol. 79, No. 12, Dec. 1990, "Optimization and Upscaling of Doxorubicin–Containing Liposomes for Clinical Use", S. Amselem, A Gabizon and Y. Barenholz.

CRC Press, Inc., 1993, Liposome Technology, 2nd Ed., edited by G. Gregoriadis, Ph.D., vol. 1, Chapter 3, p. 49, "Liposome Preparation Using High–Pressure Homogenizers", Martin M. Bradl, Dieter Bachmann, Markus Dreschler, and Kurt H. Bauer.

Elsevier Science Publishers B.V. (Biomedical Division, 1986, Laboratory Techniques in Biochemistry and Molecular Biology, vol. 3, part 2, edited by R.H. Burdon and P.H. von knippenberg, "Techniquest of Lipidology–Isolation, Analysis and Identification of Lipids", 2nd revision edition, Moris Kates.

Primary Examiner—Gollamudi S. Kishore
Attorney, Agent, or Firm—Pennie & Edmonds

[57] ABSTRACT

The present invention provides pharmaceutical compositions comprising nanoemulsions of particles comprising a lipid core which is in a solid or liquid crystalline phase at 25° C., stabilized by at least one phospholipid envelope, for the parenteral, oral, intranasal, rectal, or topical delivery of both fat-soluble and water-soluble drugs. Particles have a mean diameter in the range of 10 to 250 nm. A wide variety of drugs and oxygen transporting perfluorocarbons may be encapsulated in the particles. In addition to drug delivery vehicles, the invention provides oxygen transporting blood substitutes, and nanoemulsions for extracorporeal maintenance of tissues prior to transplantation.

39 Claims, 3 Drawing Sheets

SOLID FAT NANOEMULSIONS

This is a continuation, of application Ser. No. 08/063,613, filed May 18, 1993 now U.S. Pat. No. 5,576,016.

1. FIELD OF THE INVENTION

The present invention concerns methods and compositions for parenteral and other routes of administration for delivery of drugs. More particularly, it concerns stable lipid-in-water emulsions containing small lipid particles which are useful as delivery vehicles for both lipid-soluble and water-soluble drugs.

2. BACKGROUND OF THE INVENTION

Available vehicles for the parenteral administration of water-insoluble compounds often produce undesirable side-effects such as hemolysis, thrombophlebitis, or blood coagulation. Liposomes and oil-in-water emulsions have been promoted as potential carriers for fat-soluble materials which minimize such undesirable side-effects. However, many problems with stability and drug loading capacity have been reported using either of these delivery systems.

The use of liposomes as drug delivery systems has been known for some time, and comprehensive review articles on their properties and clinical applications are available; see, e.g., Barenholz and Amselem, in "Liposome Technology", 2nd ed., G. Gregoriadis, ed., CRC press, 1992; Lichtenberg and Barenholz, in Methods for Biochemical Analysis, 33, D. Glick, ed., 1988. A liposome is defined as a structure consisting of one or more concentric lipid bilayers separated by water or aqueous buffer compartments. These hollow structures, which have an internal aqueous compartment, can be prepared with diameters ranging from 20 nm to 10 µm. They are classified according to their final size and preparation method as: SUV, small unilamellar vesicles (0.5–50 nm); LUV, large unilamellar vesicles (100 nm); REV, reverse phase evaporation vesicles (0.5 µm); and MLV, large multilamellar vesicles (2–10 µm). Drug molecules can be either encapsulated in the enclosed aqueous space or intercalated into the lipid bilayer. However, the exact location of the drug in a liposome depends on its physicochemical characteristics and the composition of the lipids.

Although effective for sustained release and tissue localization of drugs, liposomes have the drawback that the amount of drug that can be contained therein is limited. Furthermore, difficulties are encountered in the preparation of pharmaceutically acceptable liposomal formulations with long term stability and high percentages of drug entrapment. A major limitation of all types of unilamellar vesicles or single bilayer liposomes is their low drug loading capacity for lipophilic compounds, due to their relatively low content of lipid molecules; therefore they are more suitable for entrapment of water-soluble materials. Although encapsulation of large amounts of hydrophobic drugs in multilamellar liposomes is feasible, they are not appropriate for intravenous administration due to their large size.

Emulsions are defined as heterogeneous systems of one liquid dispersed in another in the form of droplets usually exceeding 1 µm in diameter. The two liquids are immiscible and chemically unreactive or slowly reactive. An emulsion is a thermodynamically unstable dispersed system. Instability is a result of the system's tendency to reduce its free energy by separating the dispersed droplets into two liquid phases. Instability of an emulsion during storage is evidenced by creaming, flocculation (reversible aggregation), and/or coalescence (irreversible aggregation).

The use of parenteral emulsions as drug delivery systems is still comparatively rare because of the necessity of achieving stable microdroplets of less than 1 µm to prevent formation of emboli in the blood vessels. In order to increase the stability and useful lifetime of the emulsion, the dispersed lipid droplets must be coated or treated with emulsifiers or "stabilizers," which lower the free energy at the interface and decrease the tendency of droplets to coalesce. However, many emulsifiers produce deleterious side effects upon injection into the body. Due to their detergent characteristics, most of them are hemolytic agents which act as membrane solubilizers. Formulation options are severely restricted by the very limited selection of stabilizers and emulsifiers approved and safe for parenteral injection.

The water insolubility of several important drugs, such as amphotericin B, phenytoin, miconazole, cyclosporin, diazepam, and etoposide, makes their formulation for intravenous use difficult. These drugs presently are marketed in cosolvent systems such as polyethylene glycol or propylene glycol-ethanol-benzyl alcohol mixtures. However severe toxicity problems, such as thrombophlebitis, have arisen with injectable formulations of drugs dissolved in cosolvents. Alternatives to cosolvent systems are micellar solutions or emulsions; but as mentioned above, the presence of toxic surfactants in those systems makes them undesirable for intravenous administration.

3. SUMMARY OF THE INVENTION

The present invention provides pharmaceutical compositions comprising nanoemulsions of particles comprising a lipid core composed of lipid which is in a solid or liquid crystalline phase at at least 25° C., stabilized by at least one phospholipid envelope, for the parenteral, oral, rectal, intranasal, or topical delivery of both fat-soluble and water-soluble drugs. The new entity is a particulate drug vehicle which is denoted herein as a solid fat nanoemulsion or "emulsome." These compositions have features which are intermediate between liposomes and oil-in-water emulsions. Particles contain a hydrophobic core, as in standard oil-in-water emulsions, which is surrounded and stabilized by one or more layers or envelopes of phospholipid molecules, as in liposomes.

A key feature of these particles is that the core is composed of lipid which in bulk form is in a solid or liquid crystalline phase, rather than an oil in a fluid phase. Lipid compositions of the core are characterized as being in the solid or liquid crystal phase at at least 25° C. when measured in bulk form.

Emulsomes, having the characteristics of both liposomes and emulsions, provide the advantages of high hydrophobic drug loading in the internal solid lipid core and the ability to encapsulate water-soluble medicaments in the aqueous compartments of surrounding phospholipid layers. Emulsomes are particularly useful for administration of poorly water-soluble lipophilic drugs which heretofore either could not be administered parenterally or, if so administered, would cause undesirable side-effects.

The present pharmaceutically stable solid fat nanoemulsions or emulsomes may be formulated in the absence of any ionic or non-ionic nonnatural synthetic surfactant or cosurfactant such as polyoxamers, deoxycholate, polysorbates, tyloxapol, or emulphor. They are stabilized by the combination of relatively high lecithin content and the use of solid lipid compositions as the core.

The particle size distribution of emulsomes, based on differential weight percents, is in the range of 10–250 nm, making them suitable for intravenous administration. This invention is also directed to processes for making such compositions.

The use of emulsomes as a drug delivery system has demonstrable advantages, including high loading of problematic drugs that previously could not be administered intravenously in the absence of cosolvents or toxic surfactants The solid lipid nanoemulsions of this invention provide effective pharmaceutical delivery for a broad variety of both water-soluble and water-insoluble drugs with minimal local or systemic toxicity.

Examples of drugs and biological compounds that have been successfully formulated in emulsomes and shown in animal studies to provide enhanced plasma levels without deleterious side-effects include antifungal agents, AZT-derivatives, β-blockers, antiepileptic drugs, antibiotics, antineoplastic compounds, neuroprotectant agents, antiinflammatory drugs, and others.

Emulsomes containing perfluorocarbons also have been shown to be successful oxygen carriers or blood substitutes. They are also suitable for extracorporeal maintenance of living tissues, such as organs prior to transplantation.

In addition to parenteral drug delivery vehicles, the invention provides nanoemulsions for instillation into the eye, topical delivery to the lungs as aerosols or nebulae, topical delivery to the skin as a dermatological ointment, intranasal administration as droplets, and oral or rectal administration.

4. BRIEF DESCRIPTION OF THE DRAWINGS

Figure 3:
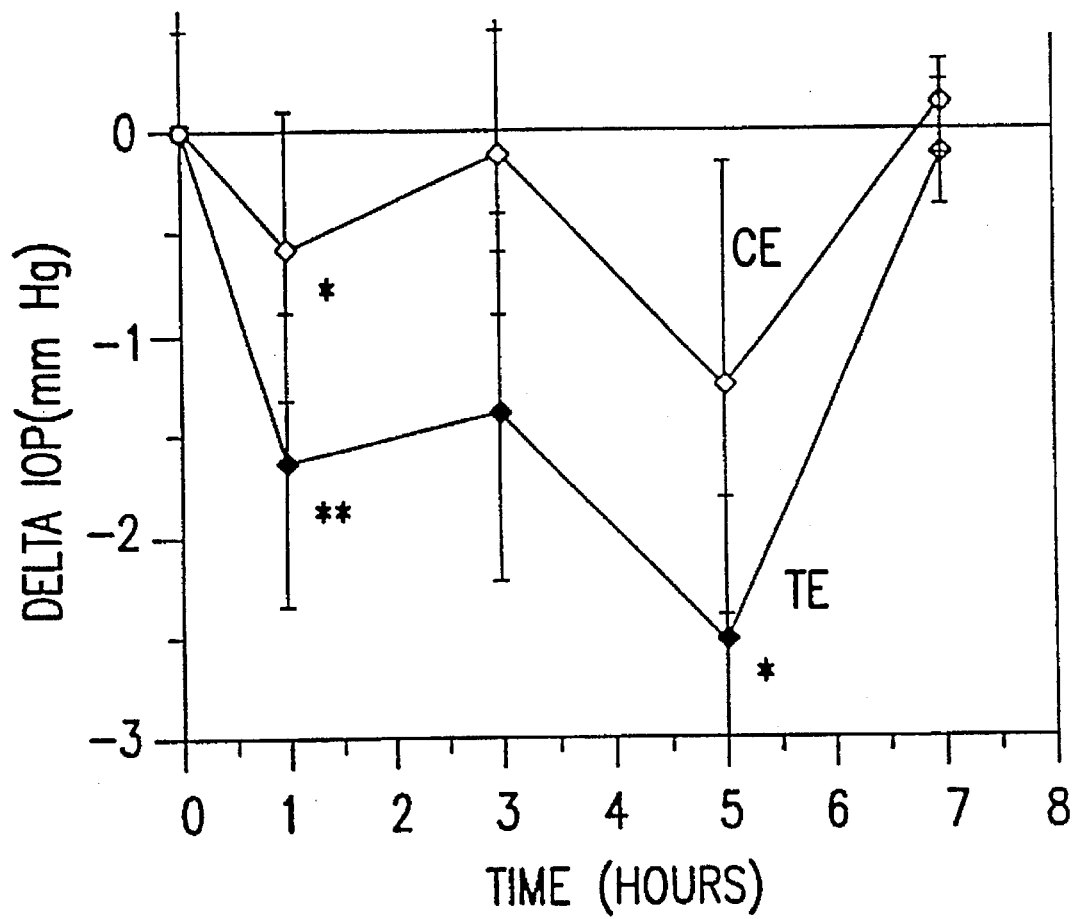

FIG. 3 is a graph showing the reduction of intraocular pressure in rabbits receiving emulsomes of Example 16 containing 0.4% adaprolol maleate. The intraocular pressure (IOP) was determined in albino rabbits (n=8 in each group) after administration of adaprolol maleate 0.4% in emulsomes to the contralateral eye (CE) and treated eye (TE) (*$P \leq 0.05$, **$p \leq 0.01$). Each value is presented as a mean±SEM.

5. DETAILED DESCRIPTION OF THE INVENTION

This invention is directed to pharmaceutical compositions for the delivery of fat-soluble and water-soluble drugs, and to methods for preparing and using such compositions.

As used herein, the term "lipid" refers to compounds which are soluble in hydrocarbon solvents and are of a structural type which includes fatty acids and their esters, cholesterol and cholesteryl esters, and phospholipids.

5.1. Composition of the Lipid Core

An essential component of emulsomes is an internal hydrophobic or lipid core comprising lipid which exhibits solid or liquid crystal or mixed solid and liquid crystal phases at room temperature (25° C.) when measured in bulk. The lipid may be a single compound or a mixture. The term "lipid" as applied to the lipid core herein may refer either to a single pure lipid compound or to a mixture of lipid compounds present in the core. Lipid compositions suitable for use as the core component of emulsomes may be characterized as being in the solid or liquid crystalline phase at at least about 25° C., when measured in bulk form without incorporation into emulsomes. Some lipid compounds present in a mixture optionally may be fluids at 25° C. when pure, provided that the lipid mixture as a whole is solid or liquid crystalline in bulk at 25° C. In preferred compositions, at least 90% of the individual lipid compounds present in the core are solids or liquid crystals at 25° C. when measured in pure bulk form.

Phase determination preferably may be performed on the bulk lipid, i.e., a macroscopic sample of the same composition, prior to its incorporation into the emulsome core. The macroscopic phase determination on a bulk sample may be made on a melting apparatus or by spectroscopic means, such as IR, NMR, or fluorescence intensity or anisotropy. Bulk phase determination of an existing emulsome preparation may be performed by first extracting the core lipids, then measuring.

Lipids which form the lipid core are composed almost exclusively of nonpolar moieties which therefore do hot exhibit a preference for the lipid-water interface. Triglycerides are the commonest type of fatty acid esters used in preparing the lipid core of nanoemulsions of this invention.

5.1.1. Triglycerides

Triglycerides are a preferred material from which the lipid core may be prepared. The triglyceride core may be composed of a single pure triglyceride, usually available as a synthetic triglyceride, or may be a mixture of several triglycerides. Fats isolated from natural sources usually are available only as mixtures of triglycerides. Such natural mixtures are suitable for preparation of emulsomes, provided that the melting characteristics of the mixture are such that they exhibit a solid or liquid crystal phase at 25° C.

Detailed summaries of the phase behavior of various pure and mixed triglycerides are available; see D. Small, "Glycerides," in: The Physical Chemistry of Lipids from Alkanes to Phospholipids, Chapter 10, Plenum Press, New York, 1985; and M. Kates, Techniques of lipidology, Chapter 1, North Holland, Amsterdam/American Elsevier Publ. Co., Inc., New York, 1972.

From the information available in these and other standard references, one skilled in the art may choose particular fats which have the requisite property of providing a solid or liquid crystal or mixed phase at 25° C. when measured in bulk. The melting properties of particular mixtures of fats may be determined readily by simple experiments.

Many triglycerides which are solid at 25° C. have fully saturated fatty acid chains. Saturated fatty acids are advantageous because they are incapable of undergoing peroxidation reactions, which lessen the acceptable storage life of oil-in-water emulsions.

Examples of solid fats suitable for the preparation of emulsomes are triglycerides composed of natural, even-numbered and unbranched fatty acids with chain lengths in the C10–C18 range, or microcrystalline glycerol triesters of saturated, even-numbered and unbranched fatty acids of natural origin such as tricaprin, trilaurin, trimyristin, tripalmitin, and tristearin. In general, any lipid component or mixture of lipid components which provides a solid phase at room temperature (25° C.) when measured in bulk is suitable for the lipid core.

Other preferred lipid core components are esters of monounsaturated fatty acids. Although monounsaturated fatty acids are capable of undergoing peroxidation, they are less reactive than typical polyunsatured fatty acids. Natural monounsaturated fatty acids have the cis configuration. In general, these are lower melting than completely saturated fatty acid esters. Usually, therefore, monounsaturated fatty acid esters will be most useful in a mixture with higher melting saturated fatty acid esters.

Other triglycerides which are solid at 25° C. include partially hydrogenated vegetable oils. Unlike naturally occurring unsaturated fatty acids, hydrogenated oils contain unsaturated bonds in the trans configuration, which is higher melting than the cis configuration. Partially hydrogenated vegetable oils yield solid vegetable shortening (e.g., CRISCO), which may be used to prepare emulsomes which are free of cholesterol or cholesteryl esters.

Triglycerides containing polyunsaturated fatty acids may be present in small amounts in the lipid core of emulsomes, provided that the resulting triglyceride mixture is in the solid or liquid crystal phase at 25° C. when measured in bulk.

In some embodiments, the lipid of the hydrophobic core may have a solid to fluid phase transition (melting) temperature between 25° C. and physiological temperature (37° C.) when measured in bulk. For example, tricaprin melts at 35°–37° C., and is wholly or predominantly in the fluid phase at physiological temperature. Tricaprin may be used to form an excellent lipid core for nanoemulsions.

The lipid core alternatively may be composed of lipids which are in the solid phase at 37° C. when measured in bulk, such as higher saturated triglycerides, e.g., tripalmitin or tristearin. Cores of mixed fluid and solid phases at 37° C. are also possible, particularly when the core contains mixtures of lipids.

5.1.2. Monoesters

The lipid or hydrophobic core of emulsomes also may be composed of or contain monoesters of fatty acids, such us waxes. In general, waxes are long chain fatty alcohol esters of fatty acids. Many waxes have suitable melting characteristics for use in emulsomes, since they are solids at 25° C. Examples include the esters from beeswax and spermaceti, such as cetyl palmitate. Preferred waxes are made from saturated or monounsaturated fatty acids and saturated or unsaturated fatty alcohols. An example of the latter is provided by arachidyl oleate.

Other satisfactory monoesters include solid monoglycerides such as glyceryl monostearate, and fatty acid esters of short chain alcohols such as ethyl stearate.

5.1.3. Cholesteryl Esters and Cholesterol

Cholesterol and cholesteryl esters optionally may be incorporated into the lipid core or the surrounding phospholipid envelope. Cholesterol and its esters change the packing structure of lipids, and in high concentrations they induce the formation of a liquid crystal phase. A liquid crystal phase may coexist with a solid phase under some conditions.

Preferred cholesteryl esters are those of saturated or monounsaturated long chain fatty acids, such as palmitoyl or oleoyl, respectively. Cholesteryl esters may be present in levels up to 50 mol % relative to the triglyceride or other solid lipid core component.

Since cholesterol has a polar alcohol group, it tends to incorporate into the envelope monolayers or bilayers rather than into the lipid core itself, and should be considered a component of the phospholipid envelope rather than of the core.

5.1.4. Antioxidants

The lipid cores of emulsion particles of this invention optionally may contain one or more antioxidants. A preferred antioxidant is α-tocopherol or its derivatives, which are members of the Vitamin E family. Other antioxidants include butylated hydroxytoluene (BHT).

Antioxidants lessen the formation of oxidative degradation products of unsaturated lipids, such as peroxides. The need for antioxidants may be lessened by preparing the lipid core from saturated fatty acids.

5.1.5. Protein Components

Lipid particles of the invention preferably do not contain serum apolipoproteins such as apo B, apo AI, apo AII, or apo E. The apo B protein has the effect of targeting intravenously administered lipid particles to certain cellular reoeptors, such as the LDL receptor on hepatocytes and certain other cells.

Lipid particles of the invention preferably also are substantially free of intracellular marker proteins, such as those associated with the intracellular cytoskeleton (e.g., actin, myosin, troponin, tubulin, vimentin, spectrin).

Lipid particles which do not contain intracellular marker proteins or serum apolipoproteins are herein described as "noncellular" particles, since they lack characteristic indicia of lipid particles present in or derived from cellular sources.

In addition, preferred preparations of emulsomes are substantially free of lipase and phospholipase enzymatic activity. As defined herein, an emulsion is "substantially free" of lipase or phospholipase activity if the emulsion lipids or phospholipids are enzymatically cleaved at a rate of less than 0.1% per day when stored at room temperature.

Other proteins and peptides optionally may be present in emulsomes. Examples of such peptides and proteins may be cyclosporin, luteinizing hormone releasing hormone (LHRH) and its analogs, calcitonin, insulin, and other synthetic or recombinant peptides. An example of natural protein is collagen, which may be used to prepare emulsomes with controlled or sustained release properties; this is described in greater detail in section 5.5 infra.

5.2. Surface Active Molecules

In lipid particles of the invention, the lipid core is surrounded by at least one envelope or layer containing phospholipid molecules. The phospholipid envelope functions as a stabilizer or surface-active agent at the lipid-water interface, thereby lowering the surface tension.

In preferred embodiments, phospholipid molecules comprise at least 90%, more preferably 95%, even more preferably at least 99% of the surface-active molecules covering the lipid core. However, other surfactants may be used in small amounts, such as the nonnatural surfactant TWEEN. The lipid core of the nanoemulsion particles may be covered or surrounded by more than one layer or envelope of surface-active molecules containing phospholipids.

In general, the surface-active phospholipid molecules are believed to form a monolayer around the lipid core of the particles, with the polar phospholipid head groups at the aqueous interface. However, particularly at higher molar ratios of phospholipid to core lipid, excess phospholipid may be available to form one or more roughly concentric bilayers which encapsulate the lipid core with its associated phospholipid monolayer. The number of bilayer envelopes is variable, and may include one, two, or many bilayers. These bilayer envelopes entrap one or more aqueous compartments which may be made to contain a water-soluble drug by creating the lipid particles in the presence of an aqueous solution of that drug.

Although the multiple concentric bilayer model of the structure of emulsomes is proposed because it accounts for the observed ability of the particles to carry high loads of both lipid-soluble and water-soluble drugs, the present invention does not depend upon and is not limited by the accuracy of the model. Other geometric relationships between the lipid core and phospholipid molecules are possible which might explain the drug carrying capacity of emulsomes of the present invention.

5.2.1. Phospholipids

The preferred phospholipids which constitute the surrounding envelopes of emulsomes are natural phospholipids such as soybean lecithin, egg lecithin, phosphatidylglycerol, phosphatidylinositol, phosphatidylethanolamine, phosphatidic acid, sphingomyelin, diphosphatidylglycerol, phosphatidylserine, phosphatidylcholine, cardiolipin, etc.; synthetic phospholipids such as dimyristoylphosphatidylcholine, dimyristoylphosphatidylglycerol, distearoylphosphatidylglycerol, dipalmitoylphosphatidylcholine, etc.; and hydrogenated or partially hydrogenated lecithins and phospholipids.

In preferred embodiments, phospholipids which form "normal" phases (i.e., ionic "head" groups facing to the external aqueous phase and lipophilic "tails" facing internally) under physiological conditions of pH and ionic strength comprise at least 50% of the total phospholipids, more preferably at least 75%, most preferably at least 90% on a molar basis. Examples of normal phase forming phospholipids are phosphatidylcholine (lecithin), phosphatidylglycerol, and phosphatidylinositol. By contrast, phosphatidylethanolamine has a tendency to form reverse phases, with the polar head groups oriented internally and the lipophilic tails oriented outwardly. Reverse phases also may be formed by cardiolipin or phosphatidic acid in the presence of $Ca^{+2}$ ions; by phosphatidic acid at pH less than 3.0; and by phosphatidylserine at pH less than 4.0.

The phospholipid component may be either saturated or unsaturated, and may have a gel to fluid phase transition temperature either above or below 25° C. Egg or soy phosphatidylcholines (egg or soy PC) are examples of phospholipids with transition temperatures well below room temperature. Dimyristoyl phosphatidylcholine (DMPC) has a transition temperature slightly below room temperature. Dipalmitoyl and distearoyl phosphatidylcholines (DPPC and DSPC) are examples of phospholipids with transition temperatures well above room temperature, and in fact even above physiological temperature (37° C.). Acceptable emulsomes may be made with these and many other phospholipids.

In general, emulsomes prepared with phospholipids which are in the gel phase at 37° C. are expected to have more rigid bilayer envelopes and longer circulation time in plasma.

Emulsomes may be prepared with molar ratios of phospholipid to total lipid in the range of 0.1 to 0.75 (10 to 75 mol %), more usually 0.1 to 0.5 (10 to 50 mol %). The molar ratio of phospholipid to core lipid typically may be in the range of 0.1:1 to 2:1, usually 0.1:1 to 1:1, often 0.2:1 to 0.9:1, frequently 0.2:1 to 0.8:1, and commonly 0.25:1 to 0.6:1.

On a weight basis, the ratio of phospholipid to core lipid usually falls in the range 0.5:1 to 1.5:1, and frequently 0.6:1 to 1.2:1.

5.2.2. Nonnatural Surfactants

Nonnatural surfactants and detergents optionally may be incorporated into emulsomes in small amounts. As used herein, the terms "nonnatural surfactants" or "detergents" include a wide variety of manmade molecules which form micelles in aqueous solution and contain both lipophilic and hydrophilic domains; however, phospholipids which belong to naturally occurring structural type are excluded from this definition, regardless of whether a particular phospholipid is obtained by synthesis or by isolation from natural sources. Examples of nonnatural surfactants include the polysorbates ("TWEEN"), sodium dodecylsulfate (SDS), polyethoxylated castor oil ("EMULPHOR"), NP-40, and numerous other synthetic molecules. In preferred embodiments, nonnatural surfactants comprise less than 10% (mol/mol) of the total surfactant, more preferably less than 5%, still more preferably less than 1%, and most preferably less than 0.1%. A significant advantage of emulsomes is that they may be prepared as a stable emulsion in the essential absence of nonnatural surfactants. Even nonnatural surfactants which have been approved for parenteral administration are prone to cause toxic or undesirable side effects, whereas the phospholipid surfactants used in emulsomes are physiologically compatible.

In experiments to determine the effect of nonnatural surfactants on emulsome structure, polysorbate (TWEEN-80) was added to an emulsome preparation at final concentrations of 0.1, 0.5, and 1% (w/v). The mean size of the resulting emulsome particles decreased from 225 nm in the absence of polysorbate to 120, 40, and 35 nm, respectively. Thus increasing concentrations of synthetic surfactants progressively decrease the particle size, and higher concentrations than those used are expected to result in formation of micelles (1–10 nm diameter).

5.2.3. Negatively Charged Lipids

Negatively charged lipid molecules such as oleic acid, or negatively charged phospholipids such as phosphatidylglycerol, phosphatidic acid, phosphatidylinositol and phosphatidylserine, can be added to the lipid phase of emulsomes to increase the zeta potential of the composition, thus stabilizing the particles. Additionally, the incorporation of these negatively charged lipid compounds in emulsomes results in the formation of phospholipid bilayers with opposing charges, thus increasing the loading of water-soluble molecules in the aqueous compartments formed by the phospholipid bilayers surrounding the lipid core. This effect results from the larger aqueous spaces between the bilayers caused by the electrostatic repulsion between them. Another beneficial role of the inclusion of negatively charged lipid molecules in emulsomes is to reduce the likelihood of particle aggregation, which minimizes destabilizing processes such as coalescence, flocculation, or fusion. Aggregation is prevented by the repulsive forces between the approaching particles.

Negatively charged phospholipids such as phosphatidylglycerol have been incorporated into liposomal formulations used in human clinical studies; see, e.g., S. Amselem et al., *J. Pharm. Sci.* (1990) 79:1045–1052; S. Amselem et al., *J. Liposome Res.* (1992) 2:93–123. The significance of zeta potential in analyzing and predicting the properties of phospholipid bilayers is discussed in L. Sai-lung, Chapter 19, Vol. 1 in "Liposome Technology," 2nd ed., G. Gregoriadis, ed., CRC Press, Boca Raton, Fla. (1993), pp. 331–342. Both lipoidal particle size and particle stability vary as a function of zeta potential. For liposomes, zeta potential and particle size increase in proportion to the content of negatively charged phospholipid, up to 50 weight % of negatively charged phospholipid.

The preferred range of negatively charged lipid in emulsome particles is 0 to 30 mol % relative to total phospholipid and charged lipid, more preferably 5 to 20 mol %, and still more preferably 7 to 15 mol %.

5.3. Incorporation of Drugs

Water-insoluble compounds may be incorporated into solid lipid nanoemulsions by dissolving them in a suitable organic solvent together with the lipid ingredients of the composition, e.g., phospholipids and solid fatty acid esters, evaporating the solvent to complete dryness, hydrating the drug-lipid mixture with the aqueous phase utilizing mechanical shaking, and homogenizing the resultant dispersion with high-shear homogenizers to final sizes in the range of 10 to 250 nm. Water-soluble drugs or active ingredients may be encapsulated or entrapped in emulsomes by dissolving them in the aqueous medium, hydrating the dry fat-phospholipid mixture with the aqueous phase containing the drug utilizing mechanical shaking, and sizing the resultant dispersion by high shear-homogenization to the desired final size range.

Drugs of interest for incorporation into emulsomes include, inter alia, nonsteroid anti-inflammatory compounds, antineoplastic compounds, antibiotics, anticonvulsants, antiepileptics, antifungals, glycosaminoglycans, hypnotics, β-adrenergic antagonists, antianxiety agents, major tranquilizers, antidepressants, corticorsteroids, anabolic steroids, estrogens, and progesterones. As used herein, the term "glycosaminoglycans" includes haparins, heparans, and low molecular weight heparins and heparans. Particular drugs within other therapeutic categories are described in standard pharmacology textbooks.

5.3.1. Antifungal Drugs

Amphotericin B has been in clinical use for more than 30 years and still remains the most effective antifungal drug available. The drug is marketed as Fungizone®, which consists of a solubilized formulation of the drug in the natural surfactant sodium deoxycholate. Its intravenous administration, however, leads to severe acute and chronic side effects such as renal tubular dysfunction, central nervous system toxicity, rigors, and chills. Several new antifungals have been developed, but none have been shown to be as effective as amphotericin B. Oil-in-water emulsions containing amphotericin B have been prepared, but they have proven to be unstable and rapidly break down with concomitant-precipitation of the drug. The amphotericin B apparently is not intercalated at the oil-water interface.

Miconazole is another antifungal agent used for the treatment of severe systemic mycotic infections. It has a lower order of toxicity compared to amphotericin B; however, anaphylactic reactions and cardiac respiratory arrests have been reported in several patients receiving intravenous doses of miconazole.

The adverse reactions reported with the above mentioned antifungal drugs were believed to result from the surfactant materials present in the available dosage forms in order to solubilize the drug, sodium deoxycholate in the case of amphotericin B (Fungizone®), and polyoxol 35 castor oil (Cremophor or Emulphor EL®) in the case of miconazole. These surfactant compounds are also known to cause pain at the site of injection and thrombophlebitis.

Amphotericin B and miconazole have been formulated successfully in emulsomes of the present invention.

5.3.2. Antiepileptic and Anticonvulsant Drugs

Phenytoin (diphenylhydantoin) or Dilantin is another example of a drug with very poor solubility in aqueous buffer. Phenytoin is an anticonvulsant drug useful in the treatment of status epilepticus of the grand mal type. It reduces the maximal activity of brain stem centers responsible for the tonic phase of grand mal seizures. It is presently marketed in a dosage form containing a cosolvent mixture of 40% propylene glycol and 10% ethanol in water for injection at very high pH. Parenteral Dilantin must be injected slowly (not exceeding 50 mg/min in adults) directly into a large vein through a large-gauge needle or intravenous catheter. Each injection of Dilantin solution must be followed by a sterile saline injection through the same needle to avoid local venous irritation due to the high alkalinity of the solution (pH 12). The addition of Dilantin to intravenous infusion is not recommended due to lack of solubility and resultant precipitation. Soft tissue irritation and inflammation have been reported after parenteral administration of Dilantin.

Formulations of emulsomes prepared according to the present invention have been found to incorporate phenytoin and other anticonvulsant and antiepileptic compounds in clinically useful drug loads which exhibit long term stability and show little or no local or systemic side effects when administered intravenously.

5.3.3. β-adrenergic Blockers

Since the introduction of Timolol for the treatment of glaucoma in the late 1970's, β-blockers have become the major class of drug for this indication. They are effective for most patients and usually do not cause any serious side effects. However, when systemic side effects do occur they can be serious, especially in patients with congestive heart failure or asthma. Adaprolol (adamantane ethyl-4(2-hydroxy-3-isopropylamino)-propoxyphenylacetate maleate salt is an adrenergic βblocking agent designed to reduce intra-ocular pressure when administered topically to the eye, but without systemic side effects. Adaprolol maleate has been designated by the inventor as a "soft β-blocker" [U.S. Pat. Nos. 4,829,086 and 5,135,926].

The hypothesis behind the soft-β-blockers is their ability following topical administration to reach the iris/ciliary body of the eye but to produce minimal blockage of systemic adrenergic β-receptors. Adaprolol maleate is rapidly metabolized in the blood to predictable inactive metabolites, therefore it has the advantage of long lasting reduction in intraocular pressure with minimal systemic side effects, as a result of rapid breakdown of the active moiety in the blood.

An important clinical disadvantage involved with adaprolol administration is it being very irritant to the eye, causing an immediate burning sensation and discomfort. Therefore efforts have been made to find an appropriate vehicle for adaprolol maleate to avoid the discomfort upon instillation to the eye.

Emulsomes have demonstrated good entrapment of adaprolol maleate resulting in effective reduction of intraocular pressure in rabbits after topical administration. When compared with adaprolol maleate in solution, emulsomes showed a lower blinking index in guinea pigs, indicating less irritability and discomfort.

5.3.4. AIDS Drugs

Zidovudine, or azidothymidine (AZT), is an approved drug for the treatment of AIDS. AZT has been shown to be useful in improving the neuropsychiatric course of AIDS encephalopathy, but the doses required to elicit this improvement cause severe anemia, which usually leads to cessation of therapy. When the drug is withdrawn in response to this neutropenia, all of the abated symptoms promptly return. Interestingly, AZT does enter the cerebrospinal fluid after oral or intravenous administration achieving significant concentrations, but unfortunately AZT poorly penetrates the blood-brain barrier. In an effort to ameliorate the prognosis of AIDS encephalopathy, the pyridinium-dihydropyridine redox based Chemical Delivery system (CDS) approach (U.S. Pat. Nos. 4,479,932; 4,829,070; 5,002,935) was applied to AZT.

AZT-CDS (Zidovudinechemical Delivery system) is a crystalline solid stable at room temperature which is a potentially useful anti-AIDS prodrug that is designed to more efficiently deliver AZT to the brain and central nervous system, while at the same time reducing systemic levels of the drug. The enhanced brain/blood ratio is expected to significantly increase the therapeutic index of the antiretroviral agent. Intravenous studies in test animals confirm these assertions and have been replicated by a number of academic and governmental laboratories (N. Bodor and M. E. Brewster, Targeted Drug Delivery, in: "Handbook of Experimental Pharmacology, vol. 100, pp 231–284, Springer-Verlag, Berlin, 1991).

The lipophilic characteristics of AZT-CDS limits its solubility in aqueous buffers and therefore lipophilic delivery vehicles are needed, including use of organic cosolvents such as DMSO-polyethyleneglycol mixtures, inclusion in macromolecular complexes like cyclodextrins, or incorporation into lipoidal carriers. AZT-CDS has been successfully incorporated into emulsomes, and significantly increased brain levels of AZT were obtained in rats after its intravenous administration.

5.4. Pharmaceutical Preparations of Emulsomes

The size range of emulsomes described in the present invention (10–250 nm) makes them suitable for parenteral delivery. The 10–250 nm range includes the mean size on a weight basis of preferred emulsome preparations. In more preferred preparations, the 10–250 nm size range includes at least 99% of the particles in the nanoemulsion, as determined on a weight basis. "Weight basis" determination here means that the weight percent rather than the number of the lipid particles within the stated diameter range is used for the size determination. In certain preparations, the mean particle size plus or minus the standard deviation falls within the range 20 to 180 nm, 40 to 160 nm, or 50 to 150 nm. In other preparations, the mean and the standard deviation falls within the range 10 to 120 nm. In still more preferred preparations, 99% of the particles in the nanoemulsion fall within one of the above size ranges, as determined on a weight basis. All of the above emulsions can be sterilized by filtration.

Emulsomes can be administered orally, topically, rectally, intranasally, parenterally, or by aerosol inhalation. Parenteral administration may be accomplished by continuous intravenous infusion or by intravenous, intramuscular, or subcutaneous injection.

A special type of preparation for topical administration is a nanoemulsion for instillation into the eye. Typically the nanoemulsion is administered as drops applied to the cornea or at the corners of the eye. Such eye drops are rather more similar to parenteral solutions than to typical preparations for topical application to the skin, due to the sensitivity of the cornea to irritation and infection. Like parenteral emulsions, preferred emulsions for instillation into the eye are sterile. Because of the small size of nanoemulsion particles, the nanoemulsions may be sterilized by filtration.

Emulsions for instillation into the eye usually are buffered to maintain a pH close to neutrality; the usual range is about pH 6 to 8. In addition, the osmolarity of the emulsion may be maintained within 20%, more preferably 10%, and most preferably 5% of physiological value.

5.5 Polymeric Coating of Emulsomes

Biodegradable polymers may be incorporated to surround or form part of the hydrophobic core of emulsomes. Polymeric emulsomes may contain biodegradable nonnatural polymers such as polyesters of lactic and glydolic acids, polyanhydrides, polycaprolactones, polyphosphazenes and polyorthoesters, or natural polymers such as gelatin, albumin, and collagen. The advantage of polymeric emulsomes is to provide controlled release for the parenteral delivery of drugs and biological compounds in a sustained dosage form.

The structure, selection, and use of degradable polymers in drug delivery vehicles have been reviewed in a recent publication (A. Domb et al., *Polymers for Advanced Technologies* (1992) 3:279–292). Further guidance to selection of polymers is available in any standard text on that topic.

In general, the ratio of polymer to lipid core (e.g., triglyceride) may be up to 50% (w/w). For the natural protein polymers such as gelatin, which swell extensively in aqueous solution, useful levels of encapsulation may be achieved with much lower amounts of polymer, such as 1% to 10% (w/w).

For most nonnatural polymers, which are soluble in organic solvents, the polymer may be codissolved with the triglyceride and phospholipid prior to the evaporation step. For natural polymers which are soluble in aqueous solution, the polymer may be dissolved in the solution used.

5.6. Emulsomes Containing Perfluorocarbons

An approach for the production of blood substitutes or oxygen carriers involves the use of perfluorocarbons. Perfluorocarbon (PFC) emulsions have had great medical promise for the past twenty years. However, this promise has not been realized due to the inability of the pharmaceutical industry to prepare safe and stable emulsions containing high percentages of PFC. The only approved PFC emulsion available, Fluosol DA-20® (Manufactured by Green Cross Corp., Japan and distributed by Alpha Therapeutic Corporation, Calif., USA), is not stable at room temperature and must be shipped and stored frozen which limits significantly its clinical use. Additionally, Fluosol DA-20 emulsion contains only 10 percent (by volume) of perfluorocarbons, which limits its oxygen transport capacity and virtually makes it a hemodiluent rather than an resuscitative fluid. The primary surfactant in Fluosol DA-20, Pluronic F-68 (or poloxamer 188) has been implicated in complement activation, a side effect observed in about 5% of patients infused, besides the additional hemolytic and toxic effects of this surfactant as previously mentioned.

Emulsomes containing perfluorocarbons may be made by combining the perfluorocarbon with the solid lipid core component and phospholipid in a dry film, adding aqueous solution to create a dispersion, and homogenizing the dispersion to the desired size range. Perfluorocarbons may be incorporated into emulsomes in large amounts, on a weight basis relative to the amount of core lipid. The resulting emulsomes have a hydrophobic core comprising a lipid or mixture of lipids which melt at a temperature greater than 25° C. and a perfluorocarbon, surrounded by at least one layer of phospholipid. They have a diameter of 10 to 250 nm, as with other emulsomes.

Perfluorocarbon emulsomes are useful in carrying oxygen to living tissue. They may be formulated as a blood substitute or extender for intravenous administration. The emulsome preparation optionally may contain any of various plasma proteins such as clotting factors, fibrinogen, albumin, antibodies, or components of the complement system. Optionally, the perfluorocarbon emulsomes may be prepared in or diluted with plasma or serum.

Perfluorocarbon emulsomes also may be used as an extracorporeal solution to oxygenate organs and tissue for transplantation or reimplantation, especially during the transit and storage time between collection and transplantation. In the case of organs with extensive vasculature such as liver, heart, and kidney, the emulsome solution optionally may be pumped through the vessels to oxygenate internal tissues by means of a small peristaltic pump.

Extracorporeal emulsions usually are buffered to maintain the pH within 0.5 unit of physiological, e.g., in the range pH 6.9 to 7.9, and preferably within 0.2 units, e.g., pH 7.2 to 7.6. Also, salts usually are added to maintain physiological osmotic pressure and to mimic the salt balance usually found in plasma.

5.7. Lyophilized Emulsomes

Emulsomes can be lyophilized by adding cryoprotectants such as sugars or amino acids, and stored as freeze-dried solid material that can be reconstituted with the aqueous medium before use.

Preferred cryoprotectants include sugars such as glucose, sucrose, lactose, maltose, and trehalose; polysaccharides such as dextrose, dextrins, and cyclodextrins; nonnatural polymers such as polyvinylpyrrolidone (PVP); and amino acids. The preferred range of cryoprotectant to emulsome phospholipid is 0.1% up to 10% (w/w).

Dehydration of an emulsome nanoemulsion yields a solid residue which may be stored for prolonged periods, and may be rehydrated to yield an emulsome nanoemulsion having an average particle size similar to that of the original nanoemulsion. The rehydrated emulsomes also retain substantial amounts of the originally incorporated drug.

The amount of water remaining in the dehydrated emulsome preparation may vary widely depending upon the type and extent of dehydration procedure employed. In general, the dehydrated emulsomes contain less than 1% water by weight, especially when dehydrated by lyophilization. However, stable dehydrated preparations may contain up to 5% water.

5.8. Distinctive Features of Emulsomes

Emulsomes of this invention are distinct from standard oil-in-water emulsions. Due to the high phospholipid content of the current invention, a monolayer of phospholipid surrounds the lipid core at the aqueous interface thereby stabilizing the emulsion. In addition, one or more bilayers or envelopes of phospholipid molecules are believed to form around the particles in many embodiments. Another major difference is that while standard oil-in-water emulsions are dispersions of one liquid into another, emulsomes are dispersions of a solid in a liquid. The main differences between oil-in-water emulsions and emulsomes are summarized in Table 1.

One major drawback of standard oil-in-water emulsions is limited drug loading. When drug encapsulation above 1% is required, a correspondingly larger oil phase (10–20%) is required to dissolve the drug. However, the high oil content reduces the stability of the emulsion, and the addition of a surfactant or cosurfactants, is necessary. Due to the detergent properties of most surfactant compounds,

TABLE 1

Major differences among a typical submicron oil-in-water emulsion (SME), a typical liposome, and an emulsome.

|  | SME | Emulsome | Liposome |
| --- | --- | --- | --- |
| Definition | dispersion of an oil in water | dispersion of a solid lipid in water | dispersion of phospholipids in water |
| Internal core | oil | solid or liquid crystalline lipid | water |
| Phospholipid content (w/v) | 0.5–2% | 5–10% | 0.1–5% |
| Nonnatural surfactant | present | usually absent | usually absent |
| Cosurfactant | present | usually absent | usually absent |
| Lipophilic drug loading | up to 10 mg/ml | up to 100 mg/ml | up to 20 mg/ml |
| PC/total lipid (mol/mol) | 0.01–0.1 | 0.1–0.5 | 0.6–1.0 | their use for parenteral administration is very limited. Many toxic reactions have been reported even with the surfactants already approved for intravenous formulations, as in the case of Fungizone® containing sodium deoxycholate, Fluosol® containing poloxamer-188 (Pluronic F-68), Vepesid (Etoposide) containing polysorbate 80 (TWEEN 80), and Monistat® (Miconazole) containing the surfactant Emulphor EL-620 or polyethoxylated castor oil. The pharmaceutically stable nanoemulsions described herein have major advantages over standard water-in-oil emulsions in that water-soluble and water insoluble drugs can be encapsulated either separately or simultaneously at high drug loadings in the absence of any nonnatural ionic or non-ionic surfactant.

Emulsomes of this invention differ from microdroplets of U.S. Pat. Nos. 4,725,442 and 4,622,219. Microdroplets, originally called monolayer vesicles, consist of spheres of organic liquid covered by one monolayer of phospholipid, while the internal core of emulsomes consists of a solid lipid. The phospholipid content of microdroplets is low (about 1.2%) forming only one monolayer, while in emulsomes the phospholipid content is high (5–10%) and in certain embodiments is believed to form several bilayers surrounding the fat core. Another major difference between microdroplets and emulsomes is that microdroplets are useful only for water-insoluble compounds, while in emulsomes, due to the high lecithin content, water-soluble as well as water-insoluble compounds can be incorporated.

6. Method of Preparation of Emulsomes

Emulsomes may be prepared by mixing phospholipids and triglycerides in a weight ratio range of 0.5:1 wherein the triglyceride has a solid to liquid phase transition temperature of greater than 25° C.; suspending the mixture in an aqueous solution at a temperature below the solid to liquid transition temperature of the triglyceride; and homogenizing or otherwise reducing the suspension to yield the emulsomes. These emulsomes comprise a nanoemulsion of lipid particles having a mean particle diameter of between about 10 nm and 250 nm, usually within the range 20 to 180 nm, and frequently within the range 50 to 150 nm. These size ranges preferably are determined on a weight percent basis, rather than a particle number basis. The cited ranges include the mean particle size. In certain embodiments, the cited ranges include the mean plus or minus the standard error, and in other embodiments the cited ranges include at least 99% of the particles as determined on a weight basis.

Conveniently, the lipid components may be dissolved in a volatile and chemically unreactive organic solvent such as dichloromethane or diethyl ether. The drug to be incorporated usually is included in the organic solution. The solvent is removed, typically under reduced pressure in a rotary evaporator or under a stream of inert gas. The resulting lipid film is hydrated and dispersed by covering and shaking with an aqueous solution. If the drug or other components were not included in the organic solution, they may be added to the aqueous hydration solution.

The lipid suspension or dispersion is then sized, typically by high shear homogenization at pressures up to 800 bar in a Gaulin-type homogenizer. High pressure Gaulin homogenization is described in detail in Brandl et al., in *Liposome Technology*, 2nd ed., G. Gregoriadis, ed., Vol. 1, Ch. 3, CRC Press, Boca Raton, Fla., (1993), pp. 49–65.

Emulsomes also may be prepared by high pressure extrusion through polycarbonate membranes. In this procedure, the sizing step on the lipid dispersion is performed using a pressure extruder, such as the stainless steel GH76-400 Extruder or Pressure Cell (Nucleopore, USA), rather than a high-shear homogenizer. The pressure extruder and the extrusion technique for liposome preparation are described in detail in S. Amselem et al., in *Liposome Technology*, 2nd ed., G. Gregoriadis, ed., Vol. 1, Ch. 28, CRC Press, Boca Raton, Fla., (1993), pp 501–525.

Due to the small size of emulsomes they can be sterilized by final sterile filtration through 200 nanometer filter membranes.

6.1. EXAMPLE 1

Emulsomes Prepared Using a High Shear Homogenizer

To a 0.5 liter round-bottomed flask, 2.5 g of egg-lecithin, 2.5 g of tricaprin, 0.1 g of cholesterol, and 0.1 g of oleic acid, and 0.01 g of tocopherol succinate were added. The lipid mixture was dissolved in 50 ml dichloromethane. The organic solvent was evaporated until complete dryness under reduced pressure using a rotary evaporator (Heidolph, Germany). To the dry lipid film 50 ml of saline were added and the mixture was then hydrated by shaking until all the lipids were homogeneously dispersed in the aqueous phase. The dispersion was homogenized for five minutes at 15,000 rpm using a Polytron PT 3000 (Kinematica, AG). The preparation was then submitted to 10–15 cycles of high shear homogenization at 800 bar using a Microlab 70 Gaulin Homogenizer. The particle size distribution of the formulation was determined using a N4MD Coulter Particle Size Analyzer (Coulter Electronics, England). The differential weight % mode of the instrument indicated the existence of a single homogeneous population of emulsomes with a mean particle diameter of 84±32 nm. The formulation was shown to be stable at room temperature for several months without changes in the mean size of the particles.

7. Entrapment of Water-Insoluble Drugs

7.1. EXAMPLE 2

Incorporation of a Neuroprotectant Drug

To a 0.5 liter round-bottomed flask, 0.5 g of HU-211 [U.S. Pat. No. 4,876,276] a psychotropically inactive synthetic cannabinoid, 2.5 g of egg-lecithin, 3.75 g of tricaprin, 0.1 g of cholesterol, and 0.1 g of oleic acid, and 0.01 g of tocopherol succinate were added. The lipid mixture was dissolved in 50 ml dichloromethane. The organic solvent was evaporated until complete dryness under reduced pressure using a rotary evaporator (Heidolph, Germany). To the dry lipid film 50 ml of saline were added and the mixture was then hydrated by shaking until all the lipids were homogeneously dispersed in the aqueous phase. The dispersion was homogenized for five minutes at 15,000 rpm using a Polytron PT 3000 (Kinematica, AG). The preparation was then submitted to 15 cycles of high shear homogenization at 800 bar using Microlab 70 Gaulin Homogenizer. The formulation was filtered through a 0.2 μm sterile filter membrane and the particle size distribution of the formulation was determined using a N4MD Coulter Particle Size Analyzer (Coulter Electronics, England). An homogeneous population of emulsomes with a mean particle diameter of 153±24 nm was obtained. Final drug loadings of 40–90% were achieved depending on the molar ratio of tricaprin to lecithin used.

7.2. EXAMPLE 3

Neuroprotection by HU-211 Incorporated in Emulsomes in NMDA Mice Neurological Model A control group of six BALB/C male mice (18–25 g) were injected subcutaneously with 50 mg/kg doses of NMDA (25 mg/ml in PBS) and their neurological scoring was recorded. To a second group 30 mg/kg doses of HU-211 in emulsome (6 mg/ml) was administered intraperitoneally 5 hours before the NMDA injection (50–60 mg/kg, subcutaneously), and the clinical neurological appearance post NMDA administration was recorded. The results presented in Table 3 show that HU-211 in emulsomes induced neuroprotection with 50% reduction in death rate and 33% reduction in neurological scoring compared to the control mice.

TABLE 3

Average clinical neurological scoring of HU-211-emulsome pretreated mice versus control mice in NMDA model.

| Treatment | Average Score | Death rate |
| --- | --- | --- |
| NMDA | 36.2 ± 22.7 | 33% |
| HU-211 in emulsome | 24.0 ± 19.3 | 17% |

7.3. EXAMPLE 4

Incorporation of a Psychotropically Active Agent in Emulsomes

To a 0.25 liter round-bottomed flask, 20 mg of HU-210 a psychotropically active synthetic cannabinoid, 0.4 g of egg-lecithin, 0.4 g of tricaprin, 0.32 g of cholesterol, and 0.35 g of oleic acid, and 36 mg of tocopherol succinate were added. The lipid mixture was dissolved in 25 ml dichloromethane. The organic solvent was evaporated until complete dryness under reduced pressure using a rotary evaporator (Heidolph, Germany). To the dry lipid film 50 ml of saline were added and the mixture was then hydrated by shaking until all the lipids were homogeneously dispersed in the aqueous phase. The preparation was submitted to 13 cycles of high shear homogenization at 800 bar using a Microlab 70 Gaulin Homogenizer. The resultant emulsome showed an homogenous population of particles with a mean diameter of 150 nm.

7.4. EXAMPLE 5

Sedative Effect of the Cannabinoid HU-210 Incorporated in Emulsomes

Two male SD rats (200–250 g) were injected intravenously with 0.08 mg/kg doses of HU-210 incorporated in emulsomes. The sedative effect of the drug, manifested by the animal remaining motionless, absence of righting reflex, and absence of deep pain sense was obtained with an onset of 5 minutes post administration and lasted for 1 hour with an emulsome HU-210 dose of 0.4 mg/kg the sedative effect lasted for 20 hours.

7.5. EXAMPLE 6

Preparation of 1% Indomethacin in Emulsomes for Ophthalmic Use

To a 0.5 liter round-bottomed flask, 0.5 g of indomethacin, 2.5 g of egg-lecithin, 2.5 g of tricaprin, 0.1 g of cholesterol, and 0.1 g of oleic acid, and 0.01 g of tocopherol succinate were added. The lipid mixture was dissolved in 50 ml dichloromethane. The organic solvent was evaporated until completed dryness under reduced pressure using a rotary evaporator (Heidolph, Germany). To the dry lipid film 50 ml of saline were added and the mixture was then hydrated by shaking until all the lipids were homogeneously dispersed in the aqueous phase. The dispersion was homogenized for two minutes at 15,000 rpm using a Polytron PT 3000 (Kinematica, AG). The preparation was then submitted to 10 cycles of high shear homogenization at 800 bar using a Microlab 70 Gaulin Homogenizer. The particle size distribution of the resultant emulsome formulation was 111±32 nm. The formulation was shown to be stable at room temperature for several months without change in the mean size of the particles.

7.6. EXAMPLE 7

Preparation of 1% Indomethacin Emulsomecream for Topical Use

To a 100 ml flask containing 18 ml of the emulsome formulation in Example 6, were added 0.05% propylparaben, 0.1 methylparaben, 0.1% EDTA, and 5 g of a 5% Carbopol 940 solution in water. The mixture was homogenized for 60 sec using the Polytron PT 3000 and then triethanolamine was added gradually until the pH of the resultant emulsome-cream was 6.0.

7.7. EXAMPLE 8

Incorporation of AZT-CDS (Zidovudinechemical Delivery System) into Emulsomes

To a 0.5 liter round-bottomed flask, 180 mg of AZT-CDs, 3.5 g of egg-lecithin, 3.5 g of tricaprin, 0.14 gr of cholesterol, and 0.14 g of oleic acid, and 0.02 g of tocopherol succinate were added. The lipid mixture was dissolved in 50 ml dichloromethane. The organic solvent was evaporated until complete dryness under reduced pressure using a rotary evaporator (Heidolph, Germany). To the dry lipid film 70 ml of saline were added and the mixture was then hydrated by shaking until all the lipids were homogeneously dispersed in the aqueous phase. The dispersion was homogenized for 5 minutes at 17,000 rpm using a Polytron PT 3000 (Kinematica, AG). The preparation was then submitted to 10 cycles of high shear homogenization at 800 bar using a Microlab 70 Gaulin Homogenizer. The particle size distribution of the resultant emulsome formulation was 48.5±33 nm. The final drug entrapment was about 70% of initial amount added.

7.8. EXAMPLE 9

Brain-Enhanced Delivery of AZT-Q by Emulsome-AZT-CDS

The acceptance of the AZT-CDS prodrug and its potential applications would be improved if an oral dosage form were available. Efforts are therefore being made to find a feasible oral dosage form for AZT-CDS. In an effort to evaluate the feasibility of different formulations to improve bioavailability of AZT-CDS from the jejunum, doses of AZT-CDS formulated in DMSO, 2-hydroxypropyl- or dimethyl β-cyclodextrins (HPCD and DMCD), liposomes, or emulsomes were administered to rats. Fasted (18 hours) male Sprague Dawley rats weighing 150–175 g were anesthetized with Ketamine:xylazine (50:5 mg/kg, i.p.)." A single midline incision was made in the stomach, the jejunum exteriorized and a single ligature.(3-0 silk) was placed 2 cm distal to the ligament of Treitz. The AZT-CDS formulated in DMCD, HPCD, liposomes, or emulsomes, was given in an injection volume of 1.32, 2.12, 6.0, and 6.0 ml/kg respectively via a 27 gauge needle (25 gauge for liposomes and emulsomes). After injection, the muscle layer was sutured with 2–3 ligatures and the skin folds were closed with 1–2 stainless steel (11 mm) wound clips. The animals were sacrificed 1 hour after the jejunal administration. The blood, brain and liver were removed, frozen immediately and the tissues homogenized within 1 to 2 days. Organs homogenates were submitted to HPLC analysis of AZT, AZT-Q (the charged quaternary pyridinium salt metabolite of AZT-CDS) and AZT-CDS.

The results obtained are presented in Table 2. The AZT-CDS formulation in emulsomes gave rise to the highest brain levels of AZT-Q and AZT 1 hour after the jejunal administration of 50 mg/kg AZT-CDS. Among all the vehicles tested, emulsomes resulted in the highest level of brain AZT-Q. It is also worth noting that the brain level of AZT-Q obtained after jejunal administration of AZT-CDS in emulsomes (2.5 µg/g) was even higher than the level obtained after intravenous administration of AZT-CDS in DMSO (2.26 µg/g) (Table 2).

TABLE 2

Comparison of brain and blood levels of AZT and AZT-Q after intrajejunal administration of AZT-CDS to rats (50 mg/kg) in various vehicles and in emulsomes compared with an intravenous dose. All data represent one hour time points.

| Treatment | Brain (µg/g) | | Blood (µg/g) | |
| --- | --- | --- | --- | --- |
|  | AZT | AZT-Q | AZT | AZT-Q |
| Intrajejunal |  |  |  |  |
| AZT-CDS (DMSO) | 0.02 | 0.00 | 1.49 | 0.00 |
| AZT-CDS (HPβCD) | 0.72 | 0.00 | 6.01 | 1.14 |
| AZT-CDS (DMβCD) | 0.93 | 0.93 | 7.11 | 3.88 |
| AZT-CDS in Emulsomes | 0.44 | 2.50 | 7.29 | 5.66 |
| Intravenous |  |  |  |  |
| AZT-CDS (DMSO) | 1.16 | 2.26 | 2.93 | 0.18 |

7.9. EXAMPLE 10

Stable Blood-Substitute Perfluorodecaline Formulation in Emulsomes

To a 0.5 liter round-bottomed flask, 20 g of perfluorodecalin, 5 g of egg-lecithin, 5 g of tricaprin, 0.2 g of cholesterol, 0.2 g of oleic acid, and 0.02 of tocopherol succinate were added. The lipid mixture was dissolved in 100 ml diethylether. The organic solvent was evaporated until complete dryness under reduced pressure using a rotary evaporator (Heidolph, Germany). To the dry lipid film 100 ml of saline were added and the mixture was then hydrated by shaking until all the lipids were homogeneously dispersed in the aqueous phase. The dispersion was homogenized for 5 minutes at 17,000 rpm using a Polytron PT 3000 (Kinematica, AG). The preparation was then submitted to 10 cycles of high shear homogenization at 800 bar using a Microlab 70 Gaulin Homogenizer. The particle size distribution of the resultant emulsome formulation was 102±16 nm. The final perfluorodecalin blood-substitute entrapment was about 100%. The particle size distribution of the formulation was followed-up with time and no change in the mean diameter size was observed over a three month Period at 4° C.

7.10. EXAMPLE 11

Perfluorotributylamine Formulation in Emulsomes

To a 0.5 liter round-bottomed flask, 20 g of perfluorotributylamine, 5 g of egg-lecithin, 5 g of tricaprin, 0.2 g of cholesterol, 0.2 g of oleic acid, and 0.02 g of tocopherol succinate were added. The lipid mixture was dissolved in 350 ml diethylether. The organic solvent was evaporated until complete dryness under reduced pressure using a rotary evaporator (Heidolph, Germany). To the dry lipid film 100 ml of saline were added and the mixture was then hydrated by shaking until all the lipid were homogeneously dispersed in the aqueous phase. The dispersion was homogenized for 5 minutes at 17,000 rpm using a Polytron PT 3000 (Kinematica, AG) The preparation was then submitted to 10 cycles of high shear homogenization at 800 bar using a Microlab 70 Gaulin Homogenizer. The particle size distribution of the resultant emulsome formulation was 83.7±43 nm. The final perfluorotributylamine entrapment was about 100%.

7.11. EXAMPLE 12

Figure 1:
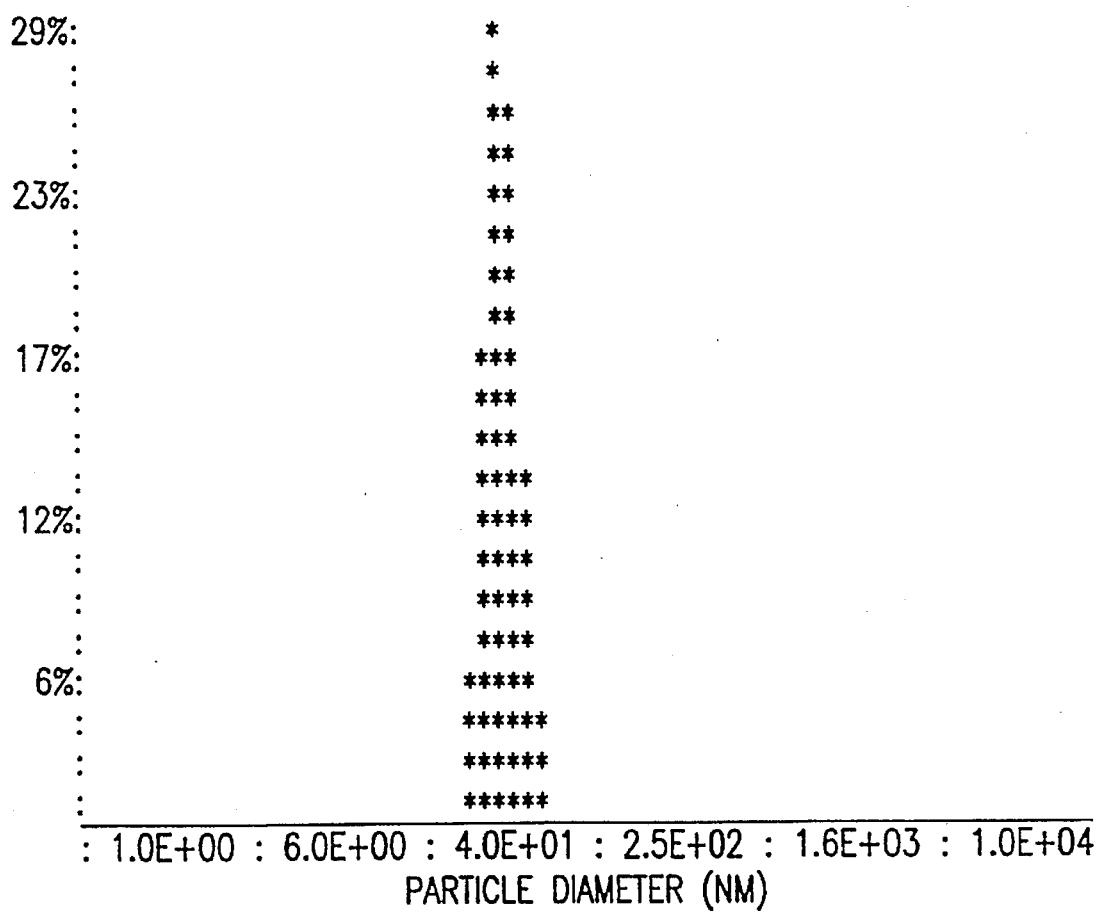
FIG. 1 is a graph showing the size distribution, as differential weight percent, of the emulsomes of Example 12 containing Amphotericin B.

Comparative Stability of Submicron Emulsion SME and Emulsome Preparations containing the Antifungal Agent Amphotericin B Emulsomes containing Amphotericin B were prepared as follows:

To a 0.5 liter round-bottomed flask, 82 mg of amphotericin B was dissolved in 100 ml methanol by bath sonication. In a separate beaker, 5 g of egg-lecithin, lecithin, 5 g of tricaprin, 0.2 g of cholesterol, 0.2 g of oleic acid, and 0.02 g of tocopherol succinate were codissolved in chloroform. Both organic solutions were mixed, glass beads (5 mm diameter) were added and the organic solvent was evaporated until complete dryness under reduced pressure using a rotary evaporator (Heidolph, Germany). To the dry lipid film 100 ml of saline were added and the mixture was then hydrated by shaking until all the lipids were homogeneously dispersed in the aqueous phase. The dispersion was homogenized for 5 minutes at 18,000 rpm using a Polytron PT 3000 (Kinematica, AG). The preparation was then submitted to 10 cycles of high shear homogenization at 800 bar using a Microlab 70 Gaulin Homogenizer. The resultant emulsomes were sterilized by filtration through a 0.45 µm membrane and stored in amber vials under a nitrogen atmosphere. The particle size distribution of the Amphotericin B emulsome preparation was determined. The nanoemulsion showed a mean particle diameter of 107±27 nm. The differential weight distribution for particles in the indicated diameter ranges is given in Table 4 and FIG. 1.

TABLE 4

Differential weight distribution by diameter for lipid particles in the Amphotericin B nanoemulsion.

| Particle Diameter (nm) | Percent of total weight |
|---|---|
| 1 | 0% |
| 2.2 | 0% |
| 4.6 | 0% |
| 10 | 0% |
| 21.5 | 0% |
| 46.4 | 0% |
| 100 | 99% |
| 215 | .8% |
| 464 | 0% |
| 1000 | 0% |
| 2150 | 0% |
| 4640 | 0% |
| 10000 | 0% |

Submicron emulsion (SME) of amphotericin B was prepared in the following way: In a 250 ml flask, 82 mg of amphotericin B was dissolved in 100 ml methanol by bath sonication. Lecithin (1.5 g) was dissolved separately in 25 ml chloroform. The amphotericin B and lecithin solutions were mixed and the organic solvents were evaporated until complete dryness using a rotary evaporator. An aqueous phase containing 2% Pluronic F68, 0.25% sodium deoxycholate, and 2.25% glycerol was prepared. The dry lipid mixture was hydrated with 100 ml of the aqueous phase and sonicated in a bath sonicator for several minutes. An oil phase containing 20 g MCT oil and 0.02 g tocopherol succinate was prepared, heated to 70° C. and added to the previous aqueous dispersion which was preheated to 45° C. Emulsification of aqueous and oil phases was then performed using the Polytron. The resultant emulsion was cooled and homogenized using the Microlab 70 Gaulin Homogenizer (10 cycles). The resultant SME-amphotericin B formulation was sterilized by filtration through a 0.45 µm membrane and stored in amber vials under a nitrogen atmosphere.

Both amphotericin B preparations in SME and emulsomes were stored at different temperatures and their stability and particle size distribution were monitored over time.

Figure 2:
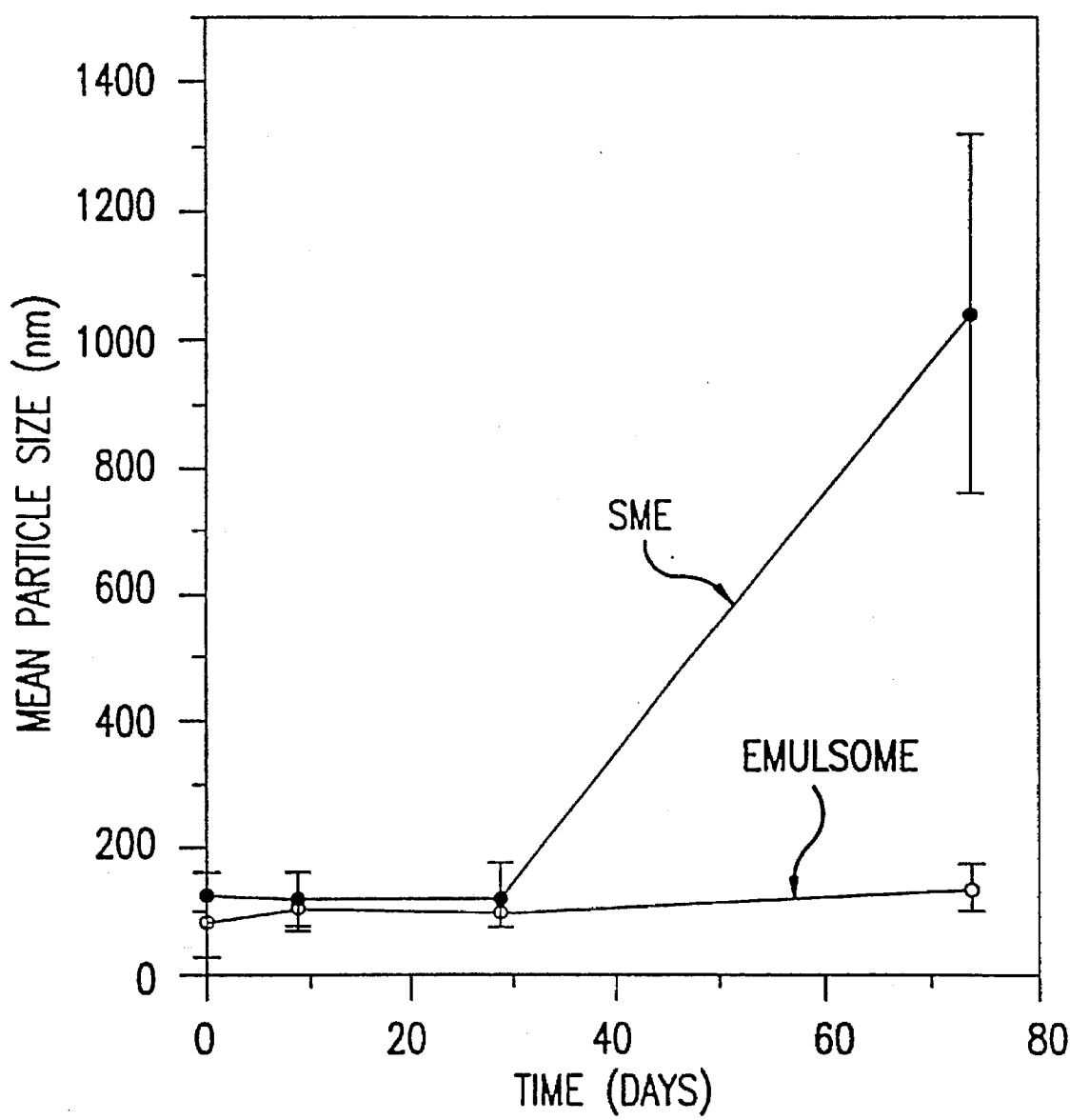
FIG. 2 is a graph showing the stability with time of the emulsomes of Example 12 containing Amphotericin B compared to a submicron oil-in-water. emulsion (SME), at 4° C.

The results obtained (see FIG. 2) show that the emulsome formulation was stable when stored at 4° C. over three months without changes in the mean particle size. However, in the case of SME a significant size increase was observed after the first month of storage under the same conditions, which resulted in emulsion breakdown and phase separation after 90 days.

7.12. EXAMPLE 13

Preparation of Emulsomes Containing Miconazole

To a 0.5 liter round-bottomed flask, 0.7 g of miconazole, 3.5 g of egg-lecithin, 5.25 g of tricaprin, 0.14 g of cholesterol, 0.14 g of oleic acid, and 0.014 g of tocopherol succinate were added. The lipid mixture was dissolved in 50 ml dichloromethane. The organic solvent was evaporated until complete dryness under reduced pressure using a rotary evaporator (Heidolph, Germany). To the dry lipid film 70 ml of saline were added and the mixture was then hydrated by shaking until all the lipids were homogeneously dispersed in the aqueous phase. The dispersion was homogenized for two minutes at 15,000 rpm using a Polytron PT 3000 (Kinematica, AG). The preparation was then submitted to 11 cycles of high shear homogenization at 800 bar using a Microlab 70 Gaulin Homogenizer. The particle size distribution of the resultant emulsome formulation was 165±90 nm.

7.13. EXAMPLE 14

Preparation of Emulsomes Containing Diazepam

To a 0.25 liter round-bottomed flask, 0.25 g of diazepam, 0.5 g of egg-lecithin, 0.43 g of tricaprin, 0.32 g trimyristin, 0.02 g of cholesterol, 0.014 g of oleic acid, and 0.008 g of tocopherol succinate were added. The lipid mixture was dissolved in 100 ml of dichloromethane. The organic solvent was evaporated until complete dryness Under reduced pressure using a rotary evaporator (Heidolph, Germany). To the dry lipid film 50 ml of saline were added and the mixture was then hydrated by shaking until all the lipids were homogeneously dispersed in the aqueous phase. The dispersion was homogenized using a Microlab 70 Gaulin Homogenizer (11 cycles at 800 bar), centrifuged at 3,000 rpm for 10 minutes, and the supernatant was filtered through a 0.2 µm filter. The particle size distribution of the resultant emulsome formulation was 91±30 nm.

7.14. EXAMPLE 15

Preparation of Emulsomes Containing Phenytoin

To a 0.5 liter round-bottomed flask, 0.7 g of sodium diphenylhydantoin (phenytoin), 3.5 g of egg-lecithin, 5.25 g of tricaprin, 0.14 g of cholesterol, and 0.14 g of oleic acid, and 0.014 g of tocopherol succinate were added. The lipid mixture was dissolved in 150 ml of methanol. The organic solvent was evaporated until complete dryness under reduced pressure using a rotary evaporator (Heidolph, Germany). To the dry lipid film 70 ml of saline were added and the mixture was then hydrated by shaking until all the lipids were homogeneously dispersed in the aqueous phase. The dispersion was homogenized using a Microlab 70 Gaulin Homogenizer (11 cycles at 800 Bar). The particle size distribution of the resultant emulsome formulation was 94±36 nm.

8. Encapsulation of Water-Soluble Drugs and Biological Agents

8.1. EXAMPLE 16

Preparation of Emulsomes Containing Adaprolol Maleate

To a 0.5 liter round-bottomed flask, 0.8 g of egg-lecithin, 0.8 g of tricaprin, 33 mg of cholesterol, 4 mg of oleic acid, and 2 mg of tocopherol succinate were added. The lipid mixture was dissolved in 100 ml of chloroform. The organic solvent was evaporated until complete dryness under reduced pressure using a rotary evaporator (Heidolph, Germany). To the dry lipid film 100 ml of phosphate buffered saline containing 0.4 g adaprolol maleate and 0.1% EDTA were added and the mixture was then hydrated by shaking until all the lipids were homogeneously dispersed in the aqueous phase. The dispersion was homogenized using a Microlab 70 Gaulin Homogenizer (13 cycles at 800 bar). The pH was adjusted to 6.5. The particle size distribution of the resultant emulsome formulation was 89±69 nm.

8.2. EXAMPLE 17

Pharmacological Effect of Emulsomes Containing Adaprolol Maleate on Intraocular Pressure in a Rabbit Model The effect of adaprolol maleate (0.4%) in the emulsome formulation of Example 16 on intraocular pressure (IOP) was studied in rabbits. Eight New Zealand adult male albino rabbits (2.5–3.0 kg) received a single dose and the IOP was measured in the rabbits at predetermined hours of the day. IOP values for each individual rabbit were recorded and defined as baseline for that time point. The changes in IOP were expressed by the IOP difference between each time point and baseline. IOP was measured using a pneumatometer (Digilab, model 3OR). IOP readings were matched with pressure readings obtained using a Digilab Calibration Verifier. As shown in FIG. 3, topical treatment with adaprolol maleate in emulsomes resulted in a significant reduction of intraocular pressure. The ocular hypotensive effect obtained lasted for 5 hours.

8.3. EXAMPLE 18

Blinking Index of Emulsomes Containing Adaprolol in Guinea Pigs Compared to Adaprolol in Solution A major side-effect of adraprolol maleate is that it causes irritability and discomfort when applied topically to the eye. The irritative response of adaprolol maleate in various ophthalmic preparations was tested in order to screen for formulations with low irritative potential. The acute irritative response was quantified using the guinea pig blinking test. In this test the number of brinks during a 5-minute period is counted following application of a 25 µl drop of test solution. Each eye is first tested with normal saline and then with the test formulation, with at least a 30-min interval between the two tests.

The blinking index is defined as the ratio of the number of blinks (drug) divided by the number of blinks(saline), and it is used as an indication of the drug irritability. As shown in Table 4, the blinking index of a 0.4% adaprolol maleate solution is 3.48. This value which reflects the irritability index of the formulation was significantly reduced to 2.00 after incorporation of the drug into the emulsome delivery system, indicating that the emulsome formulation is better tolerated by the rabbits causing less discomfort than the free drug in solution.

TABLE 5

| Blinking rate test of 0.4% adaprolol maleate in aqueous solution compared to emulsome formulation. | |
|---|---|
| Formulation | Blinking Index |
| Adaprolol in aqueous solution | 3.48 ± 0.86 |
| Adaprolol in emulsomes | 2.00 ± 0.78 |
| Plain emulsomes | 1.66 ± 0.50 |

8.4. EXAMPLE 20

Safety of Emulsomes

In order to test possible clinical toxicity of the HU-211 formulations, an animal safety study was performed. Emulsomes containing the non-psychotropic cannabinoid HU-211 were prepared as described in Example 2. Three male Sprague Dawley rats (200–300 g) were injected intravenously with 5 ml/kg doses of the emulsome formulation at a rate of 1 ml/min, using the femoral vein under light ether anesthesia. Clinical follow-up was performed for 4–5 hours following emulsome-HU-211 administration. The formulation was well tolerated by the animals and no local or systemic abnormalities were detected.

8.5. EXAMPLE 21

Lyophilization of Emulsomes

To a 0.5 liter round-bottomed flask, 180 mg of AZT-CDS, 3.5 g of egg-lecithin, 3.5 g of tricaprin, 0.14 g of cholesterol, 0.14 g of oleic acid, and 0.02 g of tocopherol succinate were added. The lipid mixture was dissolved in 50 ml dichloromethane. The organic solvent was evaporated to complete dryness under reduced pressure using a rotary evaporator (Heidolph, Germany). To the dry lipid film 70 ml of a 0.25M lactose solution were added, and the mixture was then hydrated by shaking until all the lipids were homogeneously dispersed in the aqueous phase. The dispersion was homogenized for 5 minutes at 17,000 rpm using a Polytron PT 3000 (Kinematica, AG). The preparation was then submitted to 10 cycles of high shear homogenization at 800 bar using a Microlab 70 Gaulin Homogenizer. The formulation was divided in 10 ml portions and the vials were freeze-dried using a Christ Beta Freeze Dryer (Germany). The samples were reconstituted with water for injection and the particle size distribution of the resultant reconstituted emulsome formulation was measured. An average size of 60±47 nm was measured, very similar to the mean size obtained before lyophilization.

8.6. EXAMPLE 22

Preparation of Polymeric Emulsomes for Controlled Release of Drugs

To a 0.5 liter round-bottomed flask, 0.5 g of polylactide ("Resomer L 104," MW=2,000 Da, Boehringer Ingelheim, Germany), 0.5 g of egg-lecithin, 0.5 g of tricaprin, 0.2 g of cholesterol, 0.2 g of oleic acid, and 0.02 g of tocopherol succinate were added. The lipid mixture was dissolved in 50 ml dichloromethane. The organic solvent was evaporated until complete dryness under reduced pressure using a rotary evaporator (Heidolph, Germany). To the dry lipid 50 ml of saline were added and the mixture was then hydrated by shaking until all the lipids were homogeneously dispersed in the aqueous phase. The dispersion was homogenized for 5 minutes at 17,000 rpm using a Polytron PT 3000 (Kinematica, AG). The preparation was then submitted to 10 cycles of high shear homogenization at 800 bar using a Microlab 70 Gaulin Homogenizer.

8.7. EXAMPLE 23

Scale-Up of Emulsomes

Large quantities (liters) of emulsomes were prepared according to Examples 1–22 in an industrial scale high shear homogenizer of the Molton Gaulin type. The batches obtained were shown to have the same final particle size and distribution as those obtained using the lab-scale Microlab 70 Gaulin.

9. Incorporation by Reference

To the extent necessary to understand or complete the disclosure of the present invention, all publications, patents, and patent applications mentioned herein are expressly incorporated by reference therein to the same extent as though each were individually so incorporated.

What is claimed is:

1. A nanoemulsion comprising a plurality of noncellular lipid particles having a mean diameter of about 10 to 250 nm in a pharmaceutically acceptable carrier solution, wherein each lipid particle has a core of a lipid which is in a solid phase at a temperature of at least about 25° C., said lipid core being surrounded by at least one phospholipid bilayer which has two phospholipid layers separated by an aqueous compartment.

2. The nanoemulsion of claim 1 wherein the mean particle diameter of said lipid particles falls within the range of about 20 to 180 nm.

3. The nanoemulsion of claim 2 wherein the particle diameter of at least 99% of said lipid particles falls within the range of about 50 to 150 nm.

4. The nanoemulsion of claim 2 wherein the lipid core comprises a fatty acid ester.

5. The nanoemulsion of claim 4 wherein the lipid core has a solid to fluid phase transition temperature below 37° C.

6. The nanoemulsion of claim 4 wherein the lipid core comprises a triglyceride.

7. The nanoemulsion of claim 6 wherein said triglyceride comprises a fatty acid moiety of C10 to C18.

8. The nanoemulsion of claim 6 wherein said triglyceride is completely saturated.

9. The nanoemulsion of claim 6 wherein said triglyceride is selected from the group consisting of tricaprin, trilaurin, trimyristin, tripalmitin, and tristearin.

10. The nanoemulsion of claim 6 wherein the mole ratio of phospholipid to total lipid is in the range of from 0.1:1 to 0.5:1.

11. The nanoemulsion of claim 6 wherein the weight ratio of phospholipid to triglyceride is in the range of from 0.5:1 to 1.5:1.

12. The nanoemulsion of claim 4 wherein said phospholipid comprises a phosphatidylcholine.

13. The nanoemulsion of claim 12 wherein said phosphatidylcholine is egg PC.

14. The nanoemulsion of claim 12 wherein said phosphatidylcholine has a transition temperature below 25° C.

15. The nanoemulsion of claim 12 wherein said phosphatidylcholine is saturated.

16. The nanoemulsion of claim 1 wherein said lipid particle contains cholesterol or cholesteryl esters.

17. The nanoemulsion of claim 1 wherein said lipid particle contains a drug.

18. The nanoemulsion of claim 1 wherein said lipid particle is substantially free of lipase and phospholipase activity.

19. The nanoemulsion of claim 1 wherein said lipid particle is coated with a polymer.

20. The nanoemulsion of claim 19 wherein said polymer is selected from the group consisting of polylactide, polyglycolide, polycaprolactone, gelatin, albumin, and collagen.

21. The nanoemulsion of claim 1 wherein said lipid core contains a perfluorocarbon.

22. The nanoemulsion of claim 21 wherein said perfluorocarbon is perfluorodecalin or perfluorotributylamine.

23. A composition comprising dehydrated lipid particles each having a lipid core which is in a solid phase at a temperature of about 25° C. and which is surrounded by at least one phospholipid bilayer, wherein, upon rehydration, a nanoemulsion is formed with said lipid particles having a mean diameter of about 10 to 250 nm and said bilayer comprising two phospholipid layers separated by an aqueous compartment.

24. The composition of claim 23 further comprising a cryoprotectant.

25. The composition of claim 24 wherein said cryoprotectant is selected from the group consisting of glucose, sucrose, lactose, maltose, trehalose, dextran, dextrin, cyclodextrin, polyvinylpyrrolidone, and amino acids.

26. The composition of claim 24 wherein said cryoprotectant is present in a range of from 0.1% to 10% by weight compared to lipid.

27. A method for making a nanoemulsion for administration of a drug, comprising the steps of:
  preparing a mixture comprising phospholipid and triglyceride in the weight ratio range of about 0.5:1 to 1.5:1 wherein said triglyceride has a solid to liquid phase transition temperature of greater than 25° C.;
  suspending said mixture in a aqueous solution at a temperature below the sold to liquid transition temperature of the triglyceride; and
  reducing the size of the suspension to yield a nanoemulsion of lipid particles having a mean particle diameter of between about 10 nm and 250 nm.

28. A method for delivery of a drug to an animal comprising administration to said animal of a nanoemulsion comprising a plurality of noncellular lipid particles having a mean diameter of about 50 to 250 nm, wherein each said lipid particle comprises a lipid core composed of lipid which is in a solid phase at at least about 25° C., and is surrounded by at least one phospholipid bilayer containing at least two phospholipid layers separated by a aqueous compartment, and wherein said lipid particle contains a drug.

29. The method of claim 28 wherein the drug is selected from the group consisting of nonsteroid anti-inflammatory compounds, antineoplastic compounds, antibiotics, anticonvulsants, antiepileptics, antifungals, antivirals, glycosaminoglycans, hypnotics, β-adrenergic antagonists, antianxiety agents, major tranquilizers, antidepressants, peptide hormones, corticorsteroids, anabolic steroids, estrogens, and progesterones.

30. The method of claim 28 wherein said administration is by parenteral mute.

31. The method of claim 28 wherein said administration is by oral route.

32. The method of claim 28 wherein said administration is by rectal route.

33. The method of claim 28 wherein said administration is by intranasal route.

34. The method of claim 28 wherein said administration is by topical application to skin.

35. The method of claim 28 wherein said administration is by instillation into the eye.

36. The method of claim 28 wherein said administration is by inhalation of an aerosol.

37. The method of claim 28 wherein said administration is by topical application to the skin.

38. The method of claim 28 wherein said administration is by oral route.

39. The method of claim 28 the mean diameter of said lipid particles is in the range of about 20 to 180 nm.

* * * * *